(12) United States Patent
Weisshaupt et al.

(10) Patent No.: US 10,010,325 B2
(45) Date of Patent: Jul. 3, 2018

(54) TFT COAGULATION SAFEGUARD

(71) Applicant: Aesculap AG, Tuttlingen (DE)

(72) Inventors: Dieter Weisshaupt, Immendingen (DE); Christoph Rothweiler, Donaueschingen (DE)

(73) Assignee: Aesculap AG, Tuttlingen (DE)

( * ) Notice: Subject to any disclaimer, the term of this patent is extended or adjusted under 35 U.S.C. 154(b) by 878 days.

(21) Appl. No.: 14/372,247

(22) PCT Filed: Jan. 10, 2013

(86) PCT No.: PCT/EP2013/050403
§ 371 (c)(1),
(2) Date: Jul. 15, 2014

(87) PCT Pub. No.: WO2013/107685
PCT Pub. Date: Jul. 25, 2013

(65) Prior Publication Data
US 2014/0350549 A1 Nov. 27, 2014

(30) Foreign Application Priority Data
Jan. 19, 2012 (DE) .................. 10 2012 100 425

(51) Int. Cl.
*A61B 18/12* (2006.01)
*A61B 17/11* (2006.01)
(Continued)

(52) U.S. Cl.
CPC .......... *A61B 17/11* (2013.01); *A61B 18/1233* (2013.01); *A61B 18/14* (2013.01);
(Continued)

(58) Field of Classification Search
CPC ..... A61B 17/11; A61B 18/12; A61B 18/1206; A61B 18/1233; A61B 18/14;
(Continued)

(56) References Cited

U.S. PATENT DOCUMENTS

| 2011/0152861 A1 | 6/2011 | Weisshaupt |
| 2012/0323234 A1 | 12/2012 | Weisshaupt |
| 2013/0090645 A1 | 4/2013 | Weisshaupt et al. |

FOREIGN PATENT DOCUMENTS

| DE | 4327233 A1 | 2/1995 |
| DE | 202010013150 U1 | 3/2011 |

(Continued)

OTHER PUBLICATIONS

JP Office Action with English translation for Application No. 2014-552587, dated Nov. 22, 2016, 8 pages.
Notification to attend Oral Proceeding for European Application No. 13 702 192.9, dated Nov. 22, 2017, including English translation, 10 pages.
(Continued)

*Primary Examiner* — Michael Peffley
*Assistant Examiner* — Khadijeh Vahdat
(74) *Attorney, Agent, or Firm* — RatnerPrestia

(57) ABSTRACT

A medical TFT instrument of the bipolar design includes at least two electrodes held by electrode carriers movable relative to each other which can be charged with HF current via a respective feed line. A safety switch mechanism arranged in the area of the electrode carriers and interconnected in at least one of the feed lines is additionally provided which, upon transfer of at least one of the electrode carriers into the out-of-function/situation, is brought into an OFF or disconnect position, whereby a HF current supply to the electrode associated with this feed line is disconnected.

6 Claims, 3 Drawing Sheets

(51) Int. Cl.
*A61B 18/14* (2006.01)
*A61B 18/00* (2006.01)

(52) U.S. Cl.
CPC ...... *A61B 18/1445* (2013.01); *A61B 18/1482* (2013.01); *A61B 18/1442* (2013.01); *A61B 2017/1132* (2013.01); *A61B 2018/00494* (2013.01); *A61B 2018/00619* (2013.01); *A61B 2018/126* (2013.01); *A61B 2018/1407* (2013.01); *A61B 2018/1475* (2013.01)

(58) Field of Classification Search
CPC ............ A61B 18/1442; A61B 18/1445; A61B 18/1448; A61B 18/1482; A61B 18/1496; A61B 2017/1132; A61B 2018/00494; A61B 2018/00619; A61B 2018/126; A61B 2018/1407; A61B 2018/1475
USPC ..................................................... 606/28–52
See application file for complete search history.

(56) References Cited

FOREIGN PATENT DOCUMENTS

| | | |
|---|---|---|
| DE | 202010013152 U1 | 3/2011 |
| DE | 102010020664 A1 | 11/2011 |
| WO | 9912488 A1 | 3/1999 |
| WO | 2011006937 A1 | 1/2011 |
| WO | 2011083026 | 7/2011 |
| WO | 2011083027 | 7/2011 |
| WO | 2011138347 | 11/2011 |

OTHER PUBLICATIONS

German Search Report with partial translation issued in related German Application No. 10 2012 100 425.0, dated Aug. 31, 2012.
International Search Report and Written Opinion issued in related International Application No. PCT/EP2013/050403, dated Apr. 5, 2013.

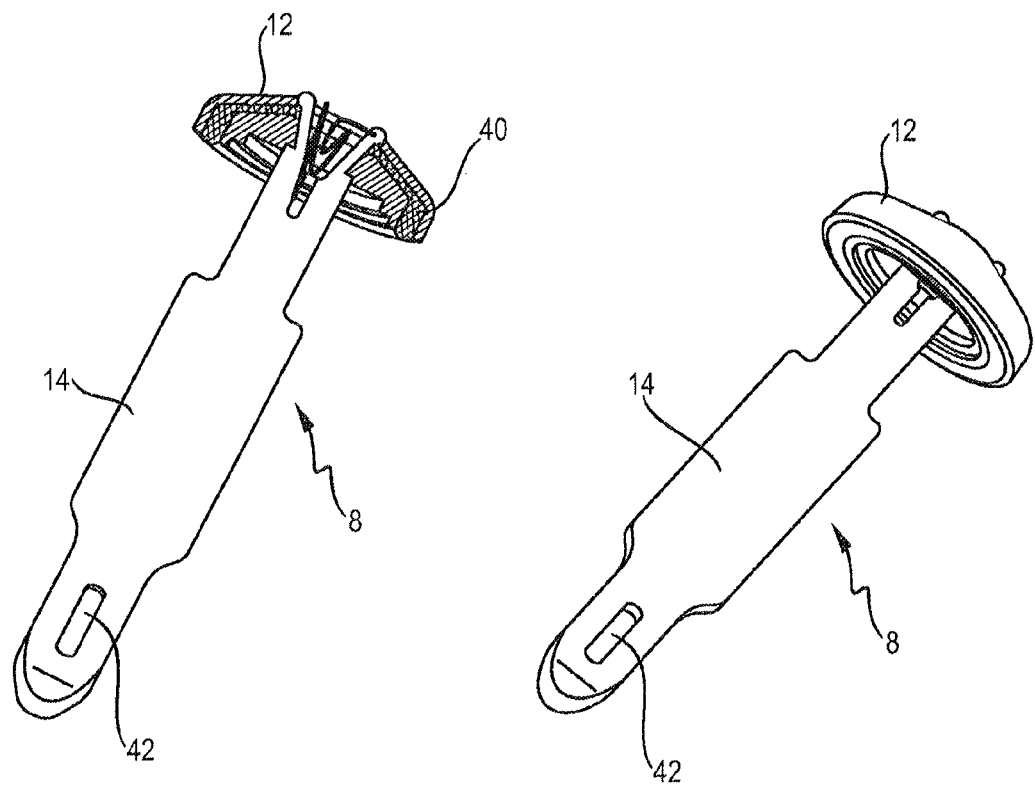
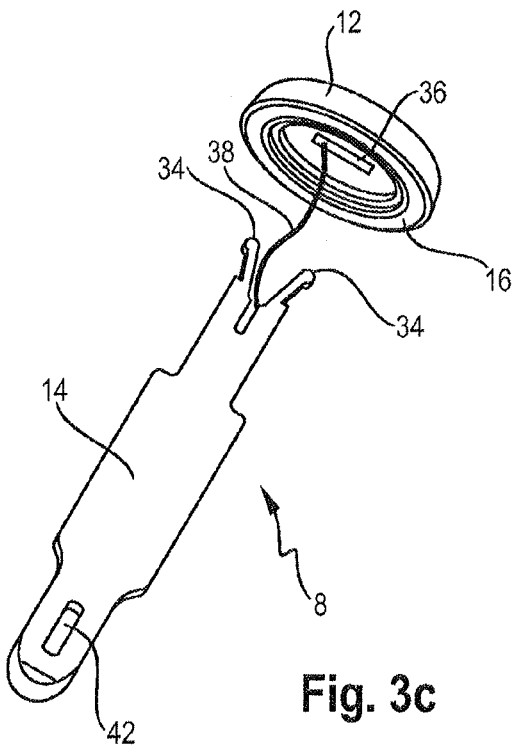
Fig. 3a    Fig. 3b
Fig. 3c

TFT COAGULATION SAFEGUARD

RELATED APPLICATIONS

This application is the U.S. National Phase of International Application No. PCT/EP2013/050403, filed Jan. 10, 2013, which claims the benefit of priority of German Application No. DE 10 2012 100 425.0, filed Jan. 19, 2012. The contents of International Application No. PCT/EP2013/050403 and German Application No. DE 10 2012 100 425.0 are incorporated by reference herein in their entirety.

FIELD

The present invention relates generally to a coagulation safeguard, and more particularly to an instrument comprising a pivotal or foldable HF electrode for end-to-end anastomosis with integrated HF power disconnection.

BACKGROUND

By end-to-end anastomosis basically an (artificial) anastomosis is understood in which two hollow organ sections (e.g. intestine parts) are re-sutured at their opened ends so that a fluid-tight and continuous course is formed. It is important in this context that the circumferential suture results in a completely fluid-tight as well as flexible and tear-resistant connection of the two hollow organ sections to be connected which is configured so that an as smooth surface as possible is formed at the inside of the hollow organ to ensure an interference-free fluid flow inside the hollow organ.

In the state of the art staple devices in the form of single-use instruments are known, as disclosed in DE 43 27 233 A1 for example. Consequently, a staple device of this type includes an endoscope shaft at the proximal end portion of which a handpiece for holding the device as well as for actuating a staple mechanism is disposed. The staple mechanism consists of a staple magazine distally fixed at the endoscope shaft approximately in the form of a cylindrical cartridge sleeve in which a number of staples circumferentially arranged on a circle are supported in a spring-biased manner as well as of a staple head or staple cap which is placed in a mushroom-like manner at the axially distal end of the cartridge sleeve and is axially movably guided in the cartridge sleeve by means of a pin fixed thereto. The stapling head is thus adapted to be continuously distanced from the cartridge sleeve in the axial direction of the staple device, thereby an adjustable circumferential (annular) axial clearance resulting between the stapling head and the cartridge sleeve, into which clearance the two ends of the hollow organ to be connected can be clamped. The staple head (or staple cap) as well as the cartridge sleeve are operable via suitable transmission means inside the endoscope shaft from the handpiece.

The problem of staple devices of this type basically consists in providing a fluid-tight as well as flexible and tear-resistant suture. For this purpose, in some staple devices two staple rows distanced in the radial direction of the cartridge sleeve are provided whose staples overlap in their engaging areas. Although the degree of tightness and the tear resistance are improved in this way, radially inwardly protruding tissue lobes or folds are necessarily formed, whereby a fluid flow inside the hollow organ can be hindered. For this reason, staple devices of this type recently have been replaced or supplemented by medical instruments, preferably having a bipolar electrode structure.

In the present case, too, such instrument includes an endoscope shaft comprising a proximal handpiece and an endoscope head preferably mechanically as well as electrically connected to the handpiece via appropriate transmission means inside the endoscope shaft. The endoscope head substantially consists of a bearing sleeve which is fixedly attached to the distal end portion of the endoscope shaft in an axially connected manner and at the distal front end of which a first circumferential electrode (electrode ring) is mounted, and of a relatively movable electrode shield (electrode cap). For this purpose, the electrode shield includes an axial pin movably guided in the bearing sleeve and coupled/adapted to be coupled to a mechanical transmission means inside the endoscope shaft for operating the same via the handpiece as well as a circumferential electrode rim arranged at the distal end of the pin on the same. The electrode rim supports, at the end face thereof facing the bearing sleeve, a second circumferential electrode (electrode ring) interacting with the first electrode.

In conformity with the staple devices known per se also in the instrument of this design, by axially moving the electrode shield through the handle an axial clearance can be set between the electrode rim and the bearing sleeve so as to clamp tissue to be connected there between and to coagulate (weld or seal) the same by charging the electrodes with HF current. By this method a flexible and fluid-tight tissue suture is formed without large tissue folds protruding into the interior of the hollow organ.

However, in instruments of this type the problem exists that at least the shield has to pass the joint without lastingly injuring the same when the instrument is removed from the hollow organ. There is always the risk that the HF current supply is inadvertently activated, whereby tissue can possibly be damaged especially in the area of the joint.

SUMMARY

In view of this problem, it is an object of the present invention to further develop a generic instrument so that the risk of inadvertent tissue damage by HF action especially when removing the instrument from an organ (preferably hollow organ) is reduced.

This object is achieved by an instrument comprising features that are described herein.

The basic idea of the invention on principle consists in guiding the HF current supply to at least one of the electrodes of a bipolar instrument according to the invention, preferably of the single-use design, via a distal safety switch mechanism (in addition to a main switch in the area of the handpiece) which safety switch mechanism is arranged (integrated) on/in at least one electrode carrier and which upon transferring the instrument or the one electrode carrier to the operating position/operating situation (situation in which the electrodes are to be supplied with current) is switched/brought automatically (i.e. automatically by moving the at least one electrode carrier) into the ON position and upon transferring the electrode carrier to the out-of-operation position/out-of-operation situation (situation in which the electrodes are no longer to be supplied with current) is switched/brought into the OFF position, thereby HF current supply being necessarily disconnected (independently of the main switch actuation). By such disconnection of the HF supply at the electrode carrier no more inadvertent tissue damage can occur, not even when HF activation is triggered by corresponding actuation at the handpiece, for example.

In the concrete case, the instrument is an end-to-end anastomosis HF instrument comprising an endoscope shaft at the distal end piece of which a substantially annular first electrode (or row of electrodes) is placed at the end face and comprising an electrode shield or electrode cap mounted at the end side of a (tubular) pin or stick which is supported to be axially movable in the distal end piece (bearing sleeve) of the endoscope shaft. The electrode cap forms sort of a rim-shaped electrode carrier which on a side facing the end piece supports a second substantially annular electrode (or row of electrodes) interacting with the first electrode.

Preferably the rim-shaped electrode carrier is centrically supported (in a hinged manner) to be foldable or pivoting on the (tubular) pin. The rim-shaped electrode carrier is pivoted or folded with respect to the pin by means of an actuating rod (needle) supported in/on the pin which is articulated to the rim-shaped electrode carrier via at least one lever, thereby an axial movement of the actuating rod along the pin being transformed into a pivoting or folding movement of the rim-shaped electrode carrier about the pin. The actuating rod is electrically connected to the electrode held by the electrode carrier (row of electrodes) and thus constitutes a portion of the HF supply. At the (tubular) pin preferably made of electrically non-conductive material a (single) contact, especially in the form of a sliding contact, is fixed (arranged/formed) which, merely at/from a predetermined axial position of the actuating rod relative to the pin in which the rim-shaped electrode carrier is substantially unfolded or swiveled into the operating position, enters into electric contact with the actuating rod or a contact provided at the latter and thus provides the HF feed line. Accordingly, the HF feed line is disconnected outside the predetermined axial position of the actuating rod relative to the pin. The actuating rod and the contact on the side of the pin thus form the safety switch mechanism according to the invention.

As an alternative, it is also possible, as a matter of course, especially in the case of a not foldable/pivoting electrode cap, to provide the safety switch mechanism between the endoscope shaft end piece (bearing sleeve) and the cap pin. In this alternative, HF current is fed to the cap-side second electrode (row of electrodes) via a feed line that is guided via the endoscope shaft end piece (bearing sleeve) and the cap pin and is closed only at/from a predetermined axial distance between the electrode cap or electrode carrier and the endoscope shaft end piece. When this predetermined axial distance (range) is exceeded or underrun, the feed line between the pin and the end piece is disconnected.

Summing up, the safety switch mechanism is accordingly coupled to a mechanical function of the HF instrument by which at least two HF electrodes are movable relative to each other so as to be brought into an operating and/or out-of-operation position.

Another alternative according to the invention provides to detachably engage, clip or clamp the electrode cap or the rim-shaped electrode carrier with/to the pin, wherein simultaneously an electric contact with the electrode on the electrode carrier side is established by this mechanical connection. I.e. the engagement/clipping/clamping at the same time constitutes also the safety switch mechanism according to the invention. In this case, the electrode carrier (electrode cap) is preferably connected to the pin by an electrically insulated or insulating thread. When the instrument is removed from/pulled out of the organ, the electrode cap is mechanically stripped off the pin (i.e. off the engagement); at the same time the electric feed line being completely disconnected at the locking mechanism. The electrode cap is then so-to-speak dragged via the electrically insulated/insulating thread. In this way, the electrode cap can be pulled through the suture made before in a comparatively simple manner, wherein no more HF current can be supplied to the electrode arranged thereon.

BRIEF DESCRIPTION OF THE DRAWING FIGURES

Hereinafter, the invention will be explained in detail by way of preferred embodiments with reference to the accompanying figures.

FIGS. 3a to 3c illustrate in detail a second variant of an axially movable electrode cap according to the invention in the operating and out-of-operation positions.

DETAILED DESCRIPTION

Figure 1:
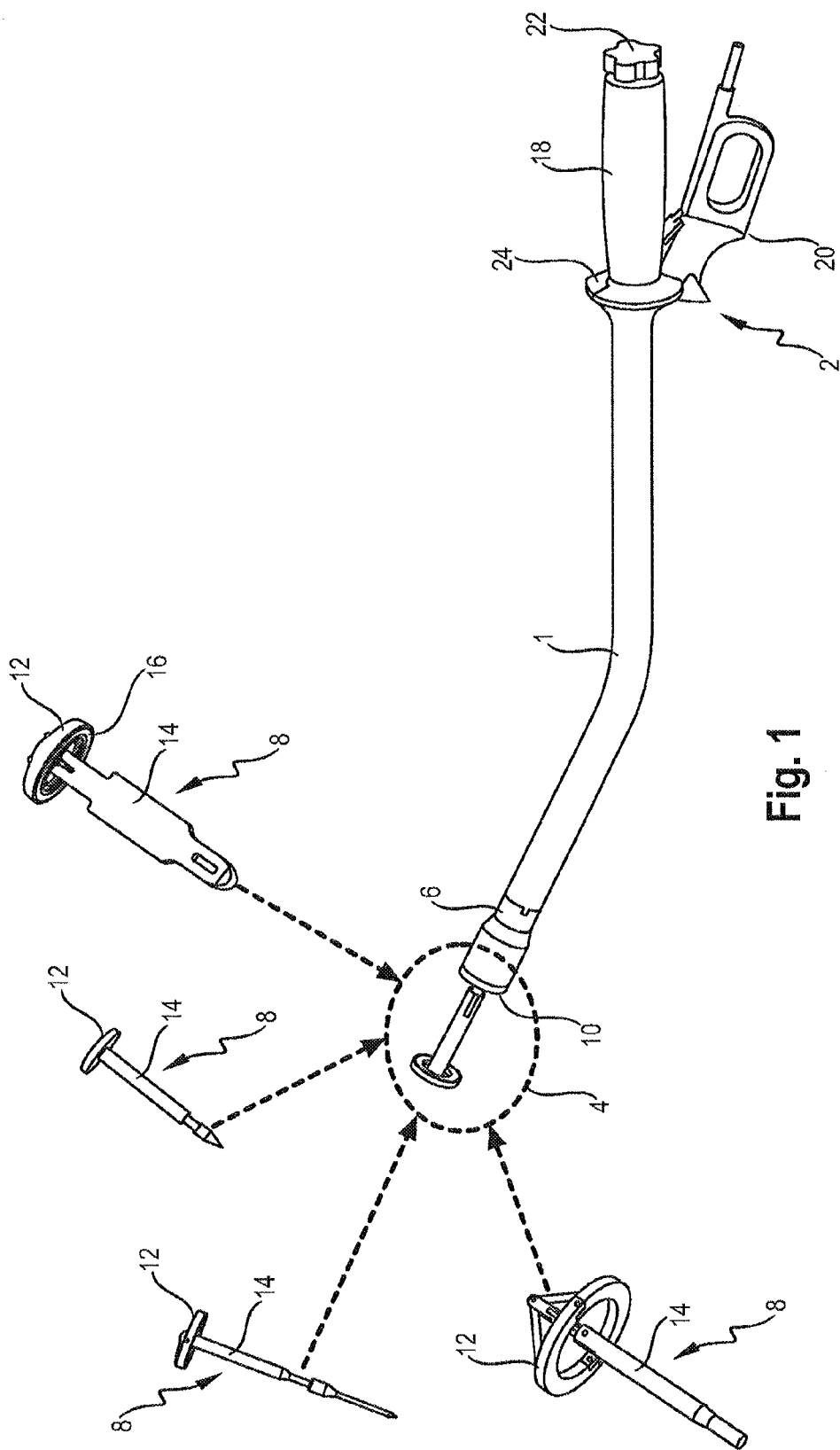
FIG. 1 illustrates a medical bipolar instrument, preferably of the end-to-end anastomosis design, comprising a number of alternative axially movable electrode caps according to the invention.

A medical instrument of bipolar design in accordance with one exemplary embodiment includes at least two electrodes being held by electrode carriers movable relative to each other which can be charged with HF current via a respective feed line. The medical instrument includes a safety switch mechanism arranged in the area of at least one of the electrode carriers and interconnected in at least one of the feed lines, which safety switch mechanism is brought into an OFF or disconnect position only upon transferring the at least one electrode carrier into the out-of-operation position or situation in which no more interaction of the two electrodes is possible or intended. HF current supply to the electrode associated with the feed line is thereby disconnected.

The medical instrument can be an end-to-end anastomosis HF instrument preferably of single-use design. In addition, the medical instrument can include a rigid endoscope shaft at the distal end piece, of which a substantially annular first electrode is placed at the end face and by an electrode cap including a pin supported to be axially movable in the distal end piece of the endoscope shaft, wherein the electrode cap supports a second substantially annular electrode interacting with the first electrode on a side facing the end piece.

The electrode cap can consist of a rim-shaped electrode carrier which is centrically supported on the now tubular pin in a hinge-like manner so as to be swiveled into an operating position substantially in parallel to the end face of the distal shaft end piece and into an out-of-function position at an angle of more than 0° with respect to the end face of the distal shaft end piece.

The safety switch mechanism can be mechanically coupled to the electrode cap and especially to the pin thereof such that at a position of the rim-shaped electrode carrier outside its operating position the at least one feed line to the electrode held by the rim-shaped electrode carrier is disconnected.

The rim-shaped electrode carrier can be pivoted relative to the pin by means of an actuating rod supported to be axially movable in the pin, the actuating rod being coupled to the rim-shaped electrode carrier via a joint lever so as to transfer an axial movement of the actuating rod along the pin into a pivoting movement of the rim-shaped electrode carrier about the pin.

The actuating rod can be electrically connected to the electrode held by the electrode carrier and thus constitutes a portion of the HF feed line, wherein at the tubular pin a contact is arranged preferably in the form of a sliding contact which at a predetermined axial position of the actuating rod relative to the pin in which the rim-shaped electrode carrier is unfolded in the operating position enters into electric contact with the actuating rod or a contact provided on the latter.

The pin can include at its distal end a snap or lock means forming the safety switch mechanism which can be mechanically engaged in a rim-shaped electrode carrier of the electrode cap so as to simultaneously establish an electric contact between the pin or a feed line arranged thereon and the electrode on the side of the electrode cap.

The electrode carrier can be connected to the pin via an electrically non-conductive thread. The at least one electrode carrier can be adapted to be brought from an operating position clamping tissue to be bonded by axial movement into an operating position releasing tissue in which the at least one electrode carrier can be transferred into the out-of-operation position by a pivoting or folding movement.

In FIG. 1, a bipolar medical instrument, preferably of the end-to-end anastomosis design, is basically shown. It is pointed out in this context, however, that the basic principle of the present invention as illustrated already in the foregoing is also applicable to medical instruments of different configuration, such as pincer-shaped coagulation instruments or scissors-shaped cutting instruments, in which at least two electrodes are movable toward each other to enter into an operating position/operating situation.

The exemplified instrument of the end-to-end anastomosis design according to FIG. 1 comprises a preferably rigid endoscope shaft 1 (i.e. more rigid than the organ tissue surrounding the same and thus not adapting to the hollow organ shape) at whose proximal end a handpiece 2 is disposed. At the distal end of the endoscope shaft 1 an endoscope head 4 is provided that substantially consists of a bearing sleeve 6 being axially fixed to or integrally formed with the endoscope shaft 1 and of an electrode cap (electrode shield) 8 being axially movably guided in the bearing sleeve 6. At the distal end face of the bearing sleeve 6 a first electrode ring (or circumferential row of electrodes) 10 is inserted which is connected via an electric feed line (not shown) passed in the endoscope shaft 1 to a proximal main switch (not shown either) in the area of the handpiece 2.

The electrode cap 8 consists of a rim-shaped electrode holder 12 that is centrally coupled to a pin 14 such that the rim-shaped electrode holder 12 can be either completely disconnected from the pin 14 or can be pivoted or folded vis-à-vis the pin 14, as will be described in detail hereinafter. The pin 14 in turn is inserted or can be inserted to be axially movable in the distal endoscope bearing sleeve 6. For operating the pivoting/folding/disconnecting mechanism and for axially moving the pin 14 within the distal bearing sleeve 6 in the endoscope shaft 1 a number of push/pull rods or Bowden cables are laid (not shown) which are coupled distally to the electrode cap 8 and proximally to the handpiece 2 and, resp., to predetermined handles of the handpiece 2. Finally a second electrode ring (or circumferential row of electrodes) 16 which is equally electrically connected/connectable to the main switch via a preferably separate feed line inside the endoscope shaft 1 is mounted on the rim-shaped electrode holder 12 to the end face thereof facing the bearing sleeve 6.

According to FIG. 1, the handpiece 2 is made of an ergonomically shaped handle 18 as well as a lever or trigger (first handle) 20 movable/pivotal relative hereto via which the integrated main switch (not shown in detail) is operable for supplying HF current to the electrodes 10, 16. Furthermore, at the handpiece 2 a number of actuating wheels or buttons (second and third handles) 22, 24 are arranged for activating the push/pull rods for axial movement of the electrode cap 8 relative to the bearing sleeve 6 as well as for operating the pivoting/folding mechanism of the rim-shaped electrode holder 12.

The general constructional design of the instrument according to the invention for mechanical coupling of the electrode cap to the endoscope shaft as well as for electric connection of the electrode to the main switch are sufficiently known from the state of the art so that in this context a further detailed description can be dispensed with. In this respect, hereinafter substantially the individual variants of the electrode caps according to the invention are described in detail by way of FIGS. 1 to 3.

As is equally evident from FIG. 1, the instrument according to the invention in the present case can be equipped with differently configured electrode caps 8 in the form of the end-to-end anastomosis instrument. Basically each electrode cap 8 includes the rim-shaped electrode holder 12 already mentioned before as well as the pin 14 extending normal hereto which is adapted to be inserted into the bearing sleeve 6 and to be coupled to an actuating means at least for axial displacement of the electrode cap 8. Depending on the design variant, the electrode holder 12 is pivoted (in a hinge-like manner) relative to the pin 14 or the electrode holder 12 is divided into several parts, each part being adapted to be folded relative to the pin 14. Alternatively, the pin 14 can be formed to include at its distal end portion an engaging or plug-in mechanism by which the rim-shaped electrode holder 12 can be locked by engagement. Said engaging/plug-in mechanism is configured so that the release direction thereof is substantially axially aligned with respect to the endoscope shaft 1 and the releasing force thereof required for disengagement is dimensioned or adjustable so that, when the instrument is removed from the hollow organ, the rim-shaped electrode holder 12 is stripped off the pin 14 and/or off the engaging/plug-in mechanism.

FIGS. 2a to 2d illustrate an electrode cap 8 of the present invention according to a first preferred embodiment in an operating and an out-of-operation position/situation.

Figure 2A:
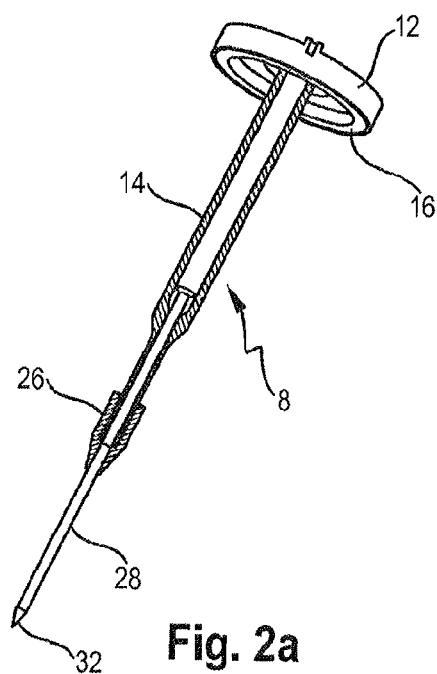
FIGS. 2a-2d illustrate in detail a first variant of an axially movable electrode cap according to the invention in the operating and out-of-operation positions.
Figure 2B:
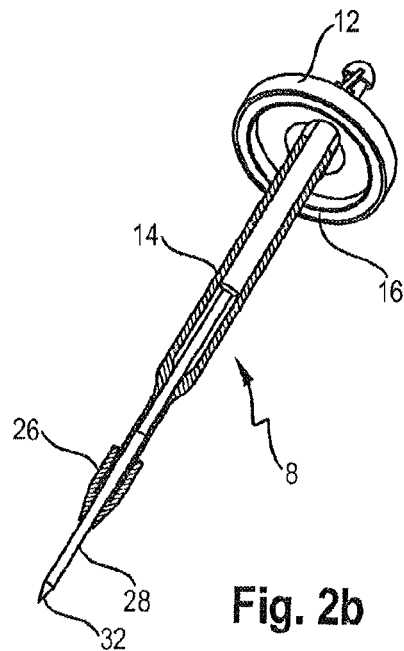
Figure 2C:
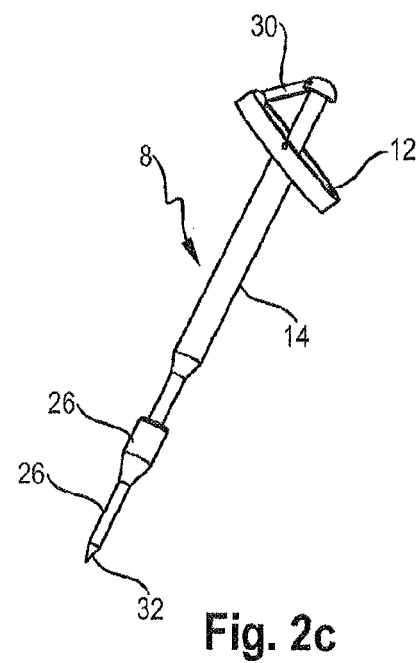
Figure 2D:
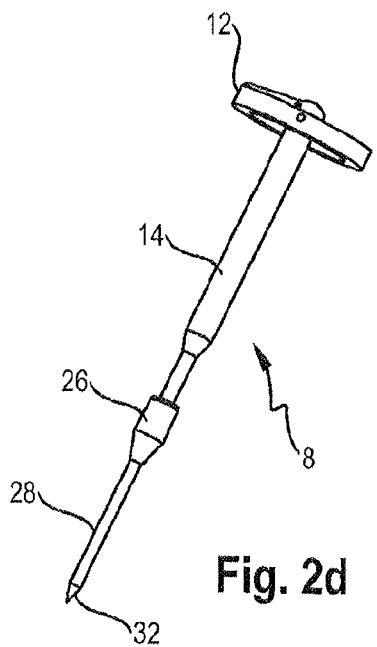

In FIG. 2a the electrode cap 8 is shown in partial longitudinal section as well as in operating position. Accordingly, the pin 14 consists of a tube made of preferably non-conductive or electrically insulating material at the distal end of which the rim-shaped electrode holder 12 is centrically hinged so that it can pivot/tilt with respect to the tubular pin 14, as illustrated in FIGS. 2b and 2c. At a proximal end portion of the tubular pin 14 an outer contact ring 26 made of electrically conductive material is fixed which preferably protrudes into portion of the interior of the tube 14. In the tube 14 an actuating rod or a needle 28 is provided in an axially movable fashion which at the distal end protrudes from the tube 14 and at the protruding distal end of which a joint lever 30 is hinged which, in turn, is articulated to the rim-shaped electrode carrier 12 on the rim side (cf. especially FIG. 2c). When, consequently, the operating rod 28 is axially displaced in the tube 14, this movement is transmitted to the electrode carrier 12, the latter tilting relative to the tube 14.

The actuating rod 28 is made of electrically conductive material (or includes an electric line) and is electrically connected to the electrode ring (circumferential row of electrodes) 16 on the electrode holder 12. The actuating rod 28 or the line mounted thereto is configured so that at a particular axial position relative to the tube 14 in which the electrode carrier 12 substantially adopts its functional position (cf. FIGS. 2a and 2d) it enters into contact with the outer contact ring 26 and thus establishes a contact connection with the electric line passed within the endoscope shaft 1. Finally the actuating rod 28 protrudes from the tube 14 also at the proximal end and at its proximal end forms an engaging portion 32 adapted to be coupled to a corresponding actuating mechanism in the endoscope shaft 1.

When, accordingly, the actuating rod 28 is displaced from the axial position (corresponding to the operating position) according to FIG. 2a or 2b, in which the electrode carrier 12 is aligned substantially in parallel to the distal end face of the bearing sleeve 6, to an axial position (corresponding to the out-of-operation position) according to FIG. 2b or 2c in which the electrode carrier 12 adopts an angle >0° relative to the distal end face of the bearing sleeve 6, at the same time the electric contact between the outer contact ring 26 and the actuating rod 28 is (automatically) disconnected so that the cap-side electrode 16 can no longer be charged with HF current. Even if at this position the main switch at the handpiece/handle 2 is (inadvertently) actuated, the cap-side electrode 16 cannot be activated. In this way damage of the surrounding tissue can be safely prevented.

It is noted in this context that the pivotal support of the rim-shaped electrode holder 12 can also be replaced with a folding support, as is schematically indicated in FIG. 1 in a variant shown there. In this case, the electrode holder 12 can be divided in two, wherein the two parts are coupled to each other in a hinge-like manner. Each part is operatively connected to the actuating rod 28 via a separate joint lever so that upon axial displacement of the actuating rod 28 the two parts can be unfolded/opened up like an umbrella.

It is also basically possible to design the electrode cap 8 without any pivoting or folding mechanism, wherein in this case the rim-shaped electrode holder 12 is tightly connected to the pin 14 (without actuating rod/needle). In such design it is possible to form the pin 14 of an electrically conductive material (whereas the electrode carrier 12 is non-conductive) and to electrically connect it to the cap-side electrode 16. The contact ring 26 then would be inserted in the bearing sleeve 6 so that in a particular axial position of the electrode cap 8 relative to the distal end face of the bearing sleeve 6 (corresponding to a particular clearance range) it enters into contact with or disconnects the contact with the pin 14.

Finally, a further variant for an electrode cap 8 according to the invention is referred to, as shown in FIGS. 3a to 3c.

In this alternative embodiment, the cap pin 14 according to FIG. 3c is tongue-shaped or wafer-shaped, wherein at its distal end portion it is separated into two spring-elastic fork arms 34. Each fork arm 34 forms an undercut or a notch constituting a respective engagement that faces toward the spreading direction of the respective fork arm 34. The rim-shaped or cup-shaped electrode holder 12 includes in its central portion a longitudinal slit 36 provided as engaging slit for the spring-elastic fork arms 34. Moreover, at the electrode holder 12 a thread 38 made of electrically non-conductive material is fixed which in turn is fastened to the cap pin 14.

The cap pin 14 is electrically conductive at least in portions, wherein also an electric line 40 leads from the cap-side electrode 12 to the longitudinal slit in the electrode carrier (not electrically conductive), as is especially illustrated in FIG. 3a. In the operating position according to FIG. 3a the pin 14 is engaged in the longitudinal slit 36 of the electrode carrier 12 via its two spring-elastic fork arms 34 so that the electrode carrier 12 is tightly connected to the pin 14 with predefined locking force. At the same time, the pin 14 is in electric contact with the cap-side electrode 16 via the spring-elastic fork arms 34. The thread 38 is wound between the fork arms 34 in this state, as this is especially shown also in FIG. 3a.

From FIG. 3b in combination with FIG. 1 one can infer that in the locked state the electrode carrier 12 is aligned substantially in parallel to the distal end face of the bearing sleeve 6, whereby between the opposed electrodes 10, 16 (circumferential rows of electrodes) an axial gap is formed. Via a through hole 42 at the proximal end of the pin 14 the electrode cap 8 is coupled to an actuating mechanism not shown in detail for axial displacement of the electrode cap 8 in the bearing sleeve 6 so that the axial clearance can be set to a particular clearance.

When the instrument is to be removed, i.e. withdrawn, from the hollow organ (not shown), the electrode holder 12 strips off the fork arms 34, as is symbolically shown in FIG. 3c. In this case, also the electric contact between the pin 14 and the cap-side electrode 16 is interrupted/disconnected. The electrode holder 12 now is suspended on the pin 14 only via the electrically non-conductive thread 38 and is thus dragged by the endoscope.

Summing up, a medical instrument of bipolar design is disclosed comprising at least two electrodes 10, 16 held by electrode carriers 6, 12 movable relative to each other which can be charged with HF current via a respective feed line. In accordance with the invention, a safety switch mechanism arranged in the area of the electrode carriers 6, 12 and interconnected in at least one of the feed lines is additionally provided which is brought into an OFF or disconnect position when at least one of the electrode carriers 12 is transferred into the out-of-operation position/situation, thereby HF current supply to the electrode associated with this feed line being disconnected.

The invention claimed is:
1. A medical instrument of bipolar design comprising:
a rigid endoscope shaft comprising a distal end piece having an end face;
an electrode cap including a pin supported to be axially moveable in the distal end piece of the endoscope shaft;
at least two electrodes comprising a first electrode and a second electrode, the first electrode held by a first electrode carrier, and the second electrode held by a second electrode carrier, the second electrode located at the electrode cap, and the first electrode located at the distal end piece;
a first feed line for feeding current to the first electrode; and
a second feed line for feeding current to the second electrode,
the first electrode carrier and second electrode carrier being movable relative to each other to enter into an operating position in which the first electrode can be charged with HF current via the first feed line, and the second electrode can be charged with HF current via the second feed line so as to interact with each other; and
a safety switch mechanism arranged in the area of at least one of the first and second electrode carriers and interconnected with at least one of the first feed line and the second feed line,
the safety switch mechanism being mechanically coupled to the electrode cap and to the pin such that the feed line to the second electrode, held by the second electrode carrier of the electrode cap, is disconnected if the safety switch mechanism is brought into an OFF or disconnect position exclusively upon transferring the second electrode carrier of the electrode cap into an out-of-operation position or situation, in which the entering of the operating position is blocked such that no more interaction between the first electrode and second electrode is possible, thereby disconnecting HF current supply to the second electrode associated with the second feed line, wherein the pin includes at its distal end a snap or lock means forming the safety switch mechanism which can be mechanically engaged in the second electrode carrier of the electrode cap so as to simultaneously establish an electric contact between the pin or a feed line arranged thereon and the second electrode, and wherein the second electrode carrier is connected to the pin via an electrically non-conductive thread.

2. The medical instrument according to claim 1, wherein the medical instrument is an end-to-end anastomosis HF instrument of single-use design.

3. The medical instrument according to claim 1, wherein the first electrode comprises a substantially annular electrode placed at the end face, wherein the electrode cap supports the second electrode, the second electrode comprising a substantially annular electrode interacting with the first electrode on a side facing the distal end piece.

4. The medical instrument according to claim 3, wherein the second electrode carrier comprises a rim-shaped electrode carrier which is centrically supported on the pin in a hinge-like manner so as to be swiveled into the operating position substantially in parallel to the end face of the distal end piece and into the out-of-operation position or situation at an angle of more than 0° with respect to the end face of the distal end piece.

5. The medical instrument according to claim 4, wherein the safety switch mechanism is mechanically coupled to the electrode cap and to the pin such that when the second electrode carrier is in the out-of-operation position or situation, the at second feed line to the second electrode is disconnected.

6. The medical instrument according to claim 1, wherein the second electrode carrier is adapted to be brought from a first position for clamping tissue to be bonded by axial movement into a second position for releasing tissue in which the second electrode carrier can be transferred into the out-of-operation position or situation by a pivoting or folding movement.

* * * * *